(12) United States Patent
Sun et al.

(10) Patent No.: US 7,729,762 B2
(45) Date of Patent: *Jun. 1, 2010

(54) ADAPTIVE ANTI-TACHYCARDIA THERAPY APPARATUS AND METHOD

(75) Inventors: Weimin Sun, Plymouth, MN (US); Bruce H. KenKnight, Maple Grove, MN (US); Martin Tze, Maplewood, MN (US); Yatheendhar Manicka, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 526 days.

This patent is subject to a terminal disclaimer.

(21) Appl. No.: 11/267,071

(22) Filed: Nov. 3, 2005

(65) Prior Publication Data

US 2006/0052829 A1    Mar. 9, 2006

Related U.S. Application Data

(63) Continuation of application No. 10/953,081, filed on Sep. 29, 2004, now Pat. No. 7,353,060, which is a continuation of application No. 10/037,622, filed on Jan. 2, 2002, now Pat. No. 6,801,806, which is a continuation of application No. 09/545,945, filed on Apr. 10, 2000, now Pat. No. 6,400,986.

(51) Int. Cl.
*A61N 1/00* (2006.01)
(52) U.S. Cl. .......................................................... 607/5
(58) Field of Classification Search ................. 607/5–28
See application file for complete search history.

(56) References Cited

U.S. PATENT DOCUMENTS

| | | | |
|---|---|---|---|
| 4,023,564 A | 5/1977 | Valiquette et al. | |
| 4,550,221 A | 10/1985 | Mabusth | |
| 4,686,332 A | 8/1987 | Greanias et al. | |
| 4,830,006 A * | 5/1989 | Haluska et al. | 607/4 |
| 4,872,459 A | 10/1989 | Pless et al. | |

(Continued)

FOREIGN PATENT DOCUMENTS

EP    0 450 943 A2    4/1991

(Continued)

OTHER PUBLICATIONS

M. S. Wathen, M.D. et al. Shock Reduction Using Antitachycardia Pacing for Spontaneous Rapid Ventricular Tachycardia in Patients with Coronary Artery Disease. *Circulation 2001*, vol. 104:796-801. © 2001 American Heart Association, Inc.

(Continued)

*Primary Examiner*—Scott M Getzow
(74) *Attorney, Agent, or Firm*—Hollingsworth & Funk, LLC

(57) ABSTRACT

A method and apparatus for delivering anti-tachycardia pacing in an adaptive manner is disclosed. A cardiac rhythm management device, such as an implantable pacemaker, having anti-tachycardia pacing capability delivers anti-tachycardia pacing therapy in accordance with a selected pacing protocol upon detection of a terminable arrhythmia. The protocol is selected from a library of available protocols. A record of the successes and failures of each available protocol in converting tachyarrhythmias is maintained in a result table for use in selecting the protocol.

20 Claims, 2 Drawing Sheets

U.S. PATENT DOCUMENTS

| | | | |
|---|---|---|---|
| 4,880,005 A | 11/1989 | Pless et al. | |
| 5,002,052 A | 3/1991 | Haluska | |
| 5,107,850 A | 4/1992 | Olive | |
| 5,144,947 A | 9/1992 | Wilson | |
| 5,158,092 A | 10/1992 | Glace | |
| 5,161,527 A | 11/1992 | Nappholz et al. | |
| 5,161,529 A | 11/1992 | Stotts et al. | |
| 5,181,511 A | 1/1993 | Nickolls et al. | |
| 5,193,550 A | 3/1993 | Duffin | |
| 5,209,229 A | 5/1993 | Gilli | |
| 5,222,493 A | 6/1993 | Sholder | |
| 5,224,475 A | 7/1993 | Berg et al. | |
| 5,251,624 A | 10/1993 | Bocek et al. | |
| 5,257,621 A * | 11/1993 | Bardy et al. | 607/5 |
| 5,312,441 A | 5/1994 | Mader et al. | |
| 5,324,310 A | 6/1994 | Greeninger et al. | |
| 5,330,505 A | 7/1994 | Cohen | |
| 5,330,508 A | 7/1994 | Gunderson | |
| 5,342,402 A | 8/1994 | Olson et al. | |
| 5,350,410 A | 9/1994 | Kleks et al. | |
| 5,379,776 A | 1/1995 | Murphy et al. | |
| 5,411,031 A | 5/1995 | Yomtov | |
| 5,425,749 A | 6/1995 | Adams | |
| 5,447,519 A * | 9/1995 | Peterson | 607/5 |
| 5,458,620 A | 10/1995 | Adams et al. | |
| 5,472,453 A | 12/1995 | Alt | |
| 5,513,644 A | 5/1996 | McClure et al. | |
| 5,548,619 A | 8/1996 | Horiike et al. | |
| 5,587,970 A | 12/1996 | Greenwood | |
| 5,662,688 A | 9/1997 | Haefner et al. | |
| 5,683,424 A | 11/1997 | Brown et al. | |
| 5,683,431 A | 11/1997 | Wang | |
| 5,685,315 A | 11/1997 | McClure et al. | |
| 5,725,559 A | 3/1998 | Alt et al. | |
| 5,755,737 A | 5/1998 | Prieve et al. | |
| 5,779,645 A | 7/1998 | Olson et al. | |
| 5,817,027 A | 10/1998 | Arand et al. | |
| 5,836,971 A | 11/1998 | Starkweather | |
| 5,844,506 A | 12/1998 | Binstead | |
| 5,846,263 A | 12/1998 | Peterson et al. | |
| 5,855,593 A | 1/1999 | Olson et al. | |
| 5,857,977 A | 1/1999 | Caswell et al. | |
| 5,871,512 A | 2/1999 | Hemming et al. | |
| 5,893,882 A | 4/1999 | Peterson et al. | |
| 5,999,854 A | 12/1999 | Deno et al. | |
| 6,064,906 A | 5/2000 | Langberg et al. | |
| 6,076,014 A | 6/2000 | Alt | |
| 6,101,414 A | 8/2000 | Kroll | |
| 6,128,529 A | 10/2000 | Esler | |
| 6,137,308 A | 10/2000 | Nayak | |
| 6,147,680 A | 11/2000 | Tareev | |
| 6,151,524 A | 11/2000 | Krig et al. | |
| 6,167,308 A | 12/2000 | Degroot | |
| 6,185,459 B1 * | 2/2001 | Mehra et al. | 607/14 |
| 6,192,273 B1 | 2/2001 | Igel et al. | |
| 6,192,275 B1 | 2/2001 | Zhu et al. | |
| 6,212,428 B1 | 4/2001 | Hsu et al. | |
| 6,221,011 B1 | 4/2001 | Bardy | |
| 6,230,055 B1 | 5/2001 | Sun et al. | |
| 6,253,102 B1 | 6/2001 | Hsu et al. | |
| 6,266,554 B1 | 7/2001 | Hsu et al. | |
| 6,270,457 B1 | 8/2001 | Bardy | |
| 6,277,072 B1 | 8/2001 | Bardy | |
| 6,280,380 B1 | 8/2001 | Bardy | |
| 6,289,248 B1 | 9/2001 | Conley et al. | |
| 6,312,378 B1 | 11/2001 | Bardy | |
| 6,336,903 B1 | 1/2002 | Bardy | |
| 6,358,203 B2 | 3/2002 | Bardy | |
| 6,368,284 B1 | 4/2002 | Bardy | |
| 6,393,316 B1 * | 5/2002 | Gillberg et al. | 600/515 |
| 6,398,728 B1 | 6/2002 | Bardy | |
| 6,400,986 B1 | 6/2002 | Sun et al. | |
| 6,418,340 B1 | 7/2002 | Conley et al. | |
| 6,440,066 B1 | 8/2002 | Bardy | |
| 6,445,949 B1 | 9/2002 | Kroll | |
| 6,449,503 B1 | 9/2002 | Hsu | |
| 6,477,422 B1 | 11/2002 | Splett | |
| 6,480,734 B1 | 11/2002 | Zhang et al. | |
| 6,490,478 B1 | 12/2002 | Zhang et al. | |
| 6,594,523 B1 | 7/2003 | Levine | |
| 6,636,764 B1 | 10/2003 | Fain et al. | |
| 6,654,639 B1 | 11/2003 | Lu | |
| 6,708,058 B2 | 3/2004 | Kim et al. | |
| 6,731,982 B1 | 5/2004 | Kroll et al. | |
| 6,882,883 B2 | 4/2005 | Condie et al. | |
| 6,885,890 B2 | 4/2005 | Spinelli et al. | |
| 6,888,538 B2 | 5/2005 | Ely et al. | |
| 6,889,079 B2 | 5/2005 | Bocek et al. | |
| 6,993,385 B1 | 1/2006 | Routh | |
| 7,031,764 B2 | 4/2006 | Schwartz et al. | |
| 7,031,771 B2 | 4/2006 | Brown et al. | |
| 7,076,289 B2 | 7/2006 | Sakar et al. | |
| 7,085,599 B2 | 8/2006 | Kim et al. | |
| 6,084,253 A1 | 9/2006 | Johnson et al. | |
| 7,103,405 B2 | 9/2006 | Sakar et al. | |
| 7,107,098 B2 | 9/2006 | Sharma et al. | |
| 7,129,935 B2 | 10/2006 | Mackey | |
| 7,130,677 B2 | 10/2006 | Brown et al. | |
| 7,130,678 B2 | 10/2006 | Ritscher et al. | |
| 7,184,815 B2 | 2/2007 | Kim et al. | |
| 7,228,173 B2 | 6/2007 | Cazares | |
| 7,277,747 B2 | 10/2007 | Cazares et al. | |
| 7,330,757 B2 | 2/2008 | Ostroff et al. | |
| 7,477,932 B2 | 1/2009 | Lee | |
| 7,558,623 B2 | 7/2009 | Fischell et al. | |
| 2003/0045908 A1 | 3/2003 | Condie et al. | |
| 2003/0120316 A1 | 6/2003 | Spinelli et al. | |
| 2003/0144700 A1 | 7/2003 | Brown et al. | |
| 2003/0191403 A1 | 10/2003 | Zhou et al. | |
| 2003/0195572 A1 | 10/2003 | Bocek et al. | |
| 2004/0167579 A1 | 8/2004 | Sharma et al. | |
| 2004/0215092 A1 | 10/2004 | Fischell et al. | |
| 2004/0215270 A1 | 10/2004 | Ritscher et al. | |
| 2004/0239650 A1 | 12/2004 | Mackey | |
| 2004/0243014 A1 | 12/2004 | Lee et al. | |
| 2004/0254613 A1 | 12/2004 | Ostroff et al. | |
| 2005/0137641 A1 | 6/2005 | Naughton | |
| 2005/0288600 A1 | 12/2005 | Zhang et al. | |
| 2006/0069322 A1 | 3/2006 | Zhang et al. | |
| 2006/0074331 A1 | 4/2006 | Kim et al. | |
| 2006/0111643 A1 | 5/2006 | Cazares | |
| 2006/0111747 A1 | 5/2006 | Cazares et al. | |
| 2006/0111751 A1 | 5/2006 | Cazares | |
| 2006/0253044 A1 | 11/2006 | Zhang et al. | |
| 2006/0281998 A1 | 12/2006 | Li et al. | |
| 2007/0049974 A1 | 3/2007 | Li et al. | |

FOREIGN PATENT DOCUMENTS

| | | |
|---|---|---|
| EP | 0 450 943 B2 | 4/1991 |
| EP | 0360412 | 3/1995 |
| EP | 0709112 | 5/1996 |
| EP | 0801960 | 10/1997 |
| EP | 1 267 993 B1 | 3/2001 |
| EP | 1112755 | 9/2005 |
| WO | WO 98/40122 | 9/1998 |
| WO | WO2006039694 | 4/2006 |

OTHER PUBLICATIONS

Martha Kerr. Shock Rate Cut 70% with ICDs Programmed to First Deliver Antitachycardia Pacing: Results of the PainFREE Rx II Trial. NewsRhythms. MedScape CRM News 2003. www.medscape.com.

Dubin, Rapid Interpretation of EKG's, 2000, Cover Publishing Company, 6$^{th}$ Edition, p. 334-345.

Mercando et al., Measurement of Differences in Timing and Sequence Between Two Ventricular Electrodes as a Means of Tachycardia Differentiation, PACE, Part II, vol. 9, Nov.-Dec. 1986, 1069-1078. (abstract only).

Office Action from U.S. Appl. No. 11/089,185 dated Nov. 3, 2009, 7 pages.

Office Action from U.S. Appl. No. 11/209,976 dated Nov. 20, 2009, 11 pages.

* cited by examiner

ADAPTIVE ANTI-TACHYCARDIA THERAPY APPARATUS AND METHOD

CROSS-REFERENCE TO RELATED APPLICATION(S)

This patent application is a continuation of U.S. patent application Ser. No. 10/953,081 filed on Sep. 29, 2004, now issued as U.S. Pat. No. 7,353,060 which is a continuation of U.S. patent application Ser. No. 10/037,622, filed on Jan. 2, 2002, now issued as U.S. Pat. No. 6,801,806 which is a continuation of U.S. patent application Ser. No. 09/545,945, filed on Apr. 10, 2000, now issued as U.S. Pat. No. 6,400,986, the specifications of which are hereby incorporated herein by reference.

FIELD OF THE INVENTION

This invention pertains to methods and systems for treating cardiac arrhythmias with anti-tachycardia pacing. In particular, the invention relates to methods and systems for delivering anti-tachycardia pacing therapy with a cardiac rhythm management device.

BACKGROUND

Tachyarrhythmias are abnormal heart rhythms characterized by a rapid heart rate, typically expressed in units of beats per minute (bpm). Examples of tachyarrhythmias include supraventricular tachycardias (SVT's) such as sinus tachycardia, atrial tachycardia, and atrial fibrillation. The most dangerous tachyarrythmias, however, are ventricular tachycardia (VT) and ventricular fibrillation (VF). Ventricular rhythms occur when an excitatory focus in the ventricle usurps control of the heart rate from the sinoatrial node. The result is rapid and irregular contraction of the ventricles out of electromechanical synchrony with the atria. Most ventricular rhythms exhibit an abnormal QRS complex in an electrocardiogram because they do not use the normal ventricular conduction system, the depolarization spreading instead from the excitatory focus directly into the myocardium. Ventricular tachycardia is characterized by distorted QRS complexes occurring at a rapid rate, while ventricular fibrillation is diagnosed when the ventricle depolarizes in a chaotic fashion with no recognizable QRS complexes. Both ventricular tachycardia and ventricular fibrillation are hemodynamically compromising, and both can be life-threatening. Ventricular fibrillation, however, causes circulatory arrest within seconds and is the most common cause of sudden cardiac death.

Cardioversion (an electrical shock delivered to the heart synchronously with the QRS complex) and defibrillation (an electrical shock delivered without synchronization to the QRS complex to terminate ventricular fibrillation) can be used to terminate most tachycardias, including SVT's, VT, and VF. The electric shock terminates the tachycardia by depolarizing all excitable myocardium which prolongs refractoriness, interrupts reentrant circuits, discharges excitatory foci. A class of cardiac rhythm management devices known as an implantable cardioverter/defibrillator (ICD) provides this kind of therapy by delivering a shock pulse to the heart when fibrillation is detected by the device.

Another type of electrical therapy for tachycardia is anti-tachycardia pacing (ATP). In ATP, the heart is competitively paced with one or more pacing pulses in an effort to interrupt reentrant circuits causing the tachycardia. Modern ICD's typically have ATP capability so that ATP therapy is delivered to the heart when a tachycardia is detected, while a shock pulse is delivered when fibrillation occurs. Although cardioversion/defibrillation will terminate tachycardia, it consumes a large amount of stored power from the battery and results in patient discomfort owing to the high voltage of the shock pulses. It is desirable, therefore, for the ICD to use ATP to terminate a tachyarrhythmia whenever possible. Generally, only cardioversion/defibrillation will terminate fibrillation and certain high rate tachycardias, while ATP can be used to treat lower rate tachycardias. An arrhythmia which is regarded as terminable by ATP therapy, based upon rate or other factors, will be referred to herein as a terminable arrhythmia.

In most ICD's with ATP capability, ventricular fibrillation (VF) is distinguished from ventricular tachycardia (VT) using rate-based criteria so that ATP or shock therapy can be delivered as appropriate. The heart rate is usually measured by detection of the time between successive R waves (i.e., ventricular depolarizations). A measured heart rate is classified as a tachycardia when the rate is in a VT zone, defined as a range of rates above a tachycardia detection rate (TDR) but below a fibrillation detection rate (FDR). A measured heart rate above the FDR, on the other hand, is in the VF zone and is classified as a fibrillation. In a typical device, a tachycardia with a heart rate in the VT zone is treated with ATP therapy in order to avoid an unnecessary painful shock to the patient, and a defibrillation shock is delivered if the pacing fails to terminate the arrhythmia. It is a primary objective of the present invention to provide a method and apparatus for delivering ATP therapy in a manner that increases the likelihood that ATP therapy will terminate an arrhythmia without resorting to a defibrillation shock.

SUMMARY OF THE INVENTION

In accordance with the invention, a cardiac rhythm management device with ATP capability is programmed to deliver ATP therapy upon detection of a tachycardia in the VT zone by employing a pacing protocol selected from a library of such protocols. The library contains a parameter set for each protocol that defines the manner in which ATP pulses are output by the device. The selection of a particular pacing protocol from the library may be based upon information contained in a result table which reflects the past results of particular protocols in terminating arrhythmias.

In one embodiment, each time a particular protocol is used in attempting to convert an arrhythmia, the success or failure of the protocol is tabulated in the result table, and a success/failure ratio is thereby maintained and associated with each protocol in the library. The device may then be programmed to select protocols from the library in an order corresponding to the success/failure ratio of each protocol in terminating an arrhythmia. A specified number of attempts with ATP therapy may made before a shock pulse is delivered, with each attempt employing a pacing protocol selected from the library in accordance with the information contained in the result table. In one embodiment, the protocol with the highest success/failure ratio is initially selected, and if the arrhythmia is not converted, the protocol with the next highest ratio is then selected. After a specified number of unsuccessful attempts with ATP therapy, a shock pulse is delivered to terminate the arrhythmia. In a further refinement of the invention, terminable arrhythmias are classified as to type based upon rate and/or the depolarization waveform morphology, and a separate result table is maintained for each type of arrhythmia. Upon detection of a particular arrhythmia type, the result table for that type is used to select the ATP protocol to be employed and is then updated with the corresponding results of the ATP therapy attempt.

In a particular embodiment, the result table is implemented with a pair of counters associated with each protocol contained in the library. After each attempt of ATP therapy using a particular protocol, the one of the counters associated with the protocol is incremented to indicate the success or failure of the protocol in terminating the arrhythmia. The information contained in the counters may then be used to calculate a success/failure ratio or some other parameter that in some way reflects the likelihood that a protocol will be successful in terminating the arrhythmia. In the case of an embodiment with separate result tables for different arrhythmia types, separate counters for each protocol are maintained for each type of arrhythmia, so that when a particular type of terminable arrhythmia is detected, the selection of the protocol is made using the counters associated with that type of arrhythmia.

DETAILED DESCRIPTION OF THE INVENTION

Figure 1:
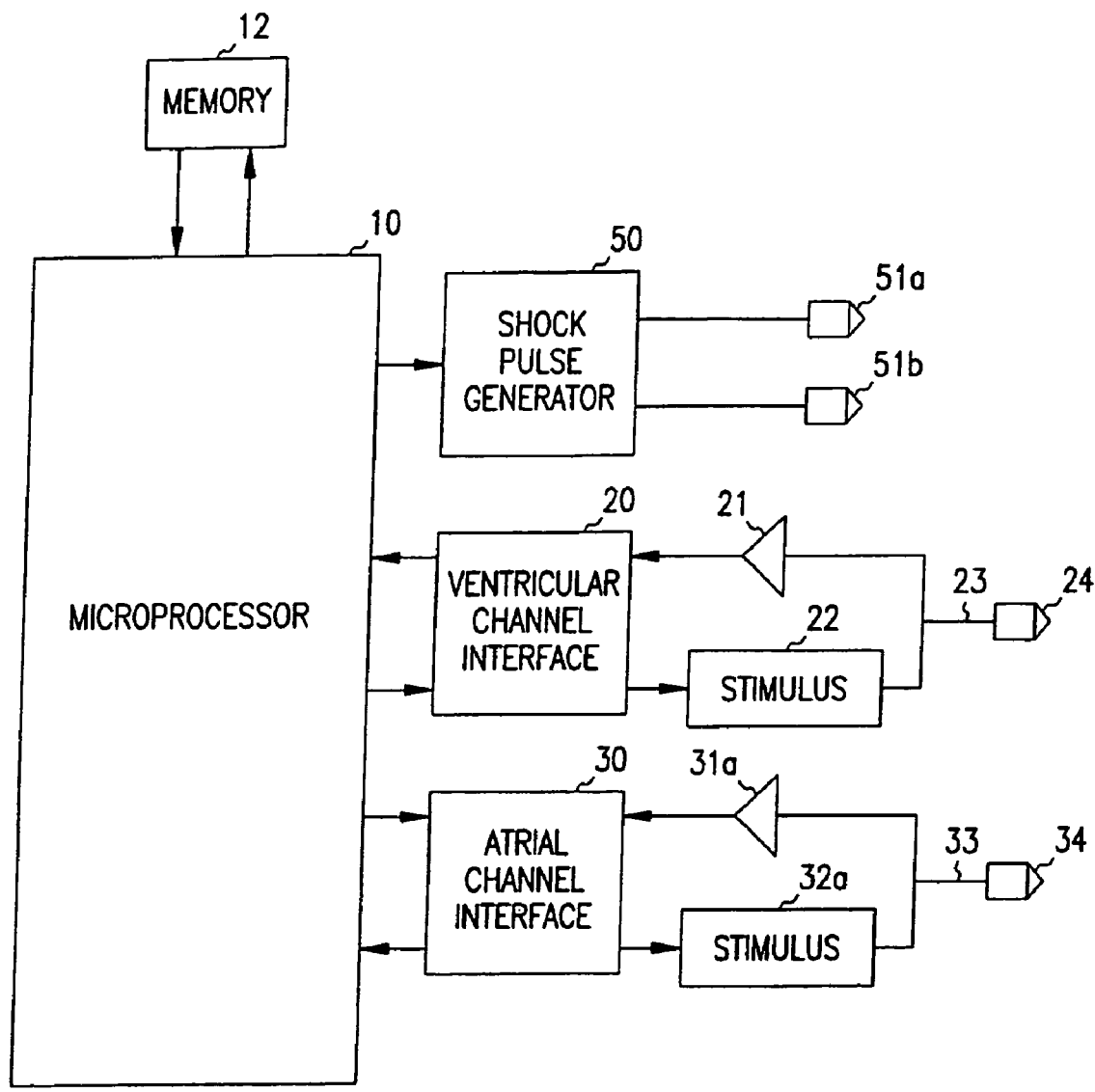
FIG. 1 is a block diagram of a cardiac rhythm management device with ATP and cardioversion/defibrillation capability.

In accordance with the invention, a cardiac rhythm management device having ATP capability is programmed with a library of pacing protocols available for delivery by the device. In a microprocessor-based device, the output of pacing pulses is controlled by a pacing routine that implements a pacing protocol as defined by various parameters. Pacing protocols for ATP therapy can generally be divided into two classes: those that deliver one or more pulses in timed relation to detected depolarizations and those that deliver a continuous pulse train for a specified time. Both types of pacing protocols attempt to reset or capture the reentrant depolarization wave front causing the tachycardia with competitive pacing pulses. Protocols of the first group may vary according to parameters that define the number of pulses delivered and the particular timing employed. Protocols of the second group include so-called burst pacing in which a short train of pulses is delivered for a specified time and may vary according to parameters that define the duration, frequency, and timing of the pulses. One type of burst pacing, called ramping, varies the frequency of the pulses up or down as the pacing is delivered. A library of pacing protocols is thus a collection of parameter sets that define these or other pacing protocols.

One way in which the library may be used is to simply program the device at the time of implantation to utilize one of the available protocols when delivering ATP therapy. Whether a given arrhythmia in the VT zone is likely to be terminated with ATP therapy, however, depends on both the design of the VT/VF zones for the detection of terminable arrhythmias and the particular pacing protocol utilized. The efficacy of a particular pacing protocol may be different, for example, for tachycardias with different heart rates. Therefore, the VT zone may be further divided into VT subzones, with a protocol selection algorithm selecting particular pacing protocols for tachycardias in different subzones. Particular pacing protocols may also be selected for application to tachycardias typed according to the morphology of the depolarization waveform. Such typing may be performed using, for example, frequency domain analysis or correlation techniques. Upon detection of a terminable arrhythmia (i.e., one deemed to be terminable by ATP therapy) of a particular type, the protocol selection algorithm can then select a particular parameter set from the library for use by the pacing routine in delivering the ATP therapy. In one implementation of an ATP protocol selection scheme, the pacing protocol is selected using a protocol selection table that associates each type of terminable arrhythmia with a protocol in the library that is regarded as most likely to be successful in terminating it. Pre-programming the protocol selection table into the device at the time of implantation, however, does not take into account that the most effective pacing protocol for a given type of arrhythmia may vary from patient to patient. Although the protocol selection table can be individualized for a given patient by testing the pacing protocols in an electro-physiology lab with induced VT's, the pacing protocols found to be most successful in terminating the induced VT's may differ markedly from the pacing protocols that would most successfully convert the spontaneous VT's that actually occur in the patient. Furthermore, putting together a pre-programmed ATP scheme requires the clinician to enter a number of interacting parameters to define the protocols and necessarily limits the number of protocols that potentially could be employed.

An improvement in accordance with the present invention is a protocol selection scheme in which ATP protocols are selected from a library in an adaptive fashion based upon a recorded history of the number of successes and failures of particular protocols in terminating detected arrhythmias. In a basic form of the invention, a list of the available protocols is maintained in the form of a table, referred to as a result table, where the results for each ATP protocol in terminating a detected terminable arrhythmia are tabulated. The result table may then be sorted in an order corresponding to the success/failure ratio of each protocol. Upon detection of terminable arrhythmia, the protocol with the highest probability of being successful, as reflected by its success/failure ratio, can then be selected from the table and used in attempting to terminate the arrhythmia. If that ATP therapy attempt fails, the next protocol in the table can be selected, with the process repeated for a specified number of times before a defibrillation shock is delivered if no ATP protocol is successful in terminating the arrhythmia. The result table is updated with the results of each ATP therapy attempt, and the table then may be re-sorted after the arrhythmia is terminated with either ATP therapy or a defibrillation shock. Alternatively, the result table may either be re-sorted after each updating of the table with a success or failure of a selected protocol or sorted at the time of each protocol selection. In an exemplary embodiment, the result table is populated with a specified number of different protocols and initialized with values corresponding to the expected probability of each protocol in terminating an arrhythmia. For example, success/failure ratio of each protocol in the result table may be set at 1:1 to reflect a 50% probability of success. The order that protocols are initially selected from the table may also be specified. After repeated ATP therapy attempts, the result table is changed to reflect the actual operating experience of the device in terminating arrhythmias and re-sorted in accordance therewith. A system incorporating the present invention is thus able to learn which protocols are the most successful in terminating arrhythmias.

The same adaptive protocol selection scheme described above may also be employed to select particular protocols for particular types of detected arrhythmias. In such an embodiment, separate result tables are maintained for each type of terminable arrhythmia classified with respect to rate and/or waveform morphology. Each result table can be populated with protocols selected specifically for a particular arrhythmia type. Then upon detection of a particular type of arrhythmia, an ATP protocol is selected from the result table for that arrhythmia type, and an attempt is made to terminate the arrhythmia with that protocol. The results are recorded in the result table for the detected arrhythmia type as a success or failure after each ATP therapy attempt, and the table is re-sorted after termination of an arrhythmia.

In the description that follows, a microprocessor-based cardiac rhythm management device will be referred to as incorporating the system and method that is the present invention. In the embodiment to be described, the invention is implemented with a control unit made up of a microprocessor executing programmed instructions in memory. It should be appreciated, however, that certain functions of a cardiac rhythm management device can be controlled by custom logic circuitry either in addition to or instead of a programmed microprocessor. The term "control unit" as used herein should therefore be taken to encompass either custom circuitry (i.e., dedicated hardware) or a microprocessor executing programmed instructions contained in a processor-readable storage medium along with associated circuit elements.

FIG. 1 is a system diagram of a microprocessor-based cardiac rhythm management device with the capability of delivering cardioversion/defibrillation shocks as well as anti-tachycardia pacing therapy. The device may also be configured to deliver conventional (e.g., bradycardia) pacing as well. The control unit of the device is a microprocessor 10 that communicates with a memory 12 via a bidirectional data bus. The memory 12 typically comprises a ROM for program storage and a RAM for data storage. The pacing routine, protocol selection algorithm, the protocol library, the result tables The device has atrial sensing and pacing channels comprising electrode 34, lead 33, sensing amplifier 31a, pulse generator 32a, and an atrial channel interface 30 which communicates bidirectionally with a port of microprocessor 10. The ventricular sensing and pacing channels similarly comprise electrode 24, lead 23, sensing amplifier 21, pulse generator 22, and a ventricular channel interface 20. For each channel, the same lead and electrode are used for both sensing and pacing. The sensing and pacing channels are used for anti-tachycardia pacing and for measuring heart rate in order to detect tachycardia and fibrillation. The microprocessor 10 analyzes the signals received from the sensing channels to detect and type arrhythmias and controls the operation of the pacing channels in order to deliver ATP therapy in accordance with a selected protocol. A shock pulse generator 50 is also interfaced to the microprocessor for delivering cardioversion or defibrillation pulses to the heart via a pair of electrodes 51a and 51b.

The device delivers ATP therapy or a defibrillation shock under programmed control of the microprocessor in response to sensed activity from the sensing channels. A sensing routine analyzes the electrical activity received from the sensing channels in order to detect an arrhythmia, and the arrhythmia is then classified as a tachycardia (i.e., a terminable arrhythmia) or fibrillation based upon rate. The device detects a ventricular tachyarrhythmia, for example, by measuring a heart rate via the ventricular sensing channel and determining whether the rate exceeds a selected threshold value. Once a tachyarrhythmia is detected, the rhythm is classified into either a tachycardia or a fibrillation by comparing the heart rate to a fibrillation rate boundary. A detected VT, for example, may then be further classified as to type by VT subzone and/or waveform morphology. The detected depolarization waveform morphology is analyzed by correlation or frequency domain techniques in order to classify the morphology of waveform. For example, a ventricular rhythm detected in the fibrillation zone may nonetheless be regarded as a terminable VT if the waveform morphology indicates that the arrhythmia is a VT and not a fibrillation.

If the arrhythmia is classified as terminable, a pacing routine executed by the microprocessor controls the output of ATP pulses in accordance with protocol parameters stored in the protocol library. The protocol library is a data structure in memory containing a plurality of pacing parameter sets, each of which is accessible by the pacing routine using a protocol identifier. For each terminable arrhythmia type that is to be detectable by the device, one or more pacing protocols are designated as available for use by the pacing routine in attempting to terminate the arrhythmia with ATP therapy. For each terminable arrhythmia type, a result table is defined in memory that contains a list of the identifiers for the designated protocols. The result table is a data structure that is used to record the successes and failures of a protocol in terminating detected arrhythmias so that the protocol with the greatest probability of terminating an arrhythmia can be selected for the ATP therapy attempt. One way of implementing this is to maintain a count of the number of successes and failures of each protocol in terminating arrhythmias with a pair of counters associated with each protocol. A success/failure ratio can be calculated for each protocol in the table, and the result table can then be sorted on the basis of the success/failure ratio so that protocols can be selected from the table in order upon detection of a terminable arrhythmia. Alternatively, the table can be searched for the protocol identifier with the highest ratio whenever a protocol is to be selected. Thus when a terminable arrhythmia is detected and typed, a protocol selection routine selects a protocol identifier from that type's result table with the highest success/failure ratio. The pacing routine then uses the selected identifier to access a parameter set from the protocol library and deliver ATP therapy employing those parameters. The result table is updated after each delivery ATP therapy by incrementing one of the counters associated with the particular protocol employed. If the therapy is successful in terminating the arrhythmia, the device returns to a monitoring mode. If the arrhythmia is not terminated, the protocol identifier with the next highest success/failure ratio is selected from the result table, either by searching the table or selecting the next identifier in a sorted table, and ATP therapy is tried again with the new protocol. If the arrhythmia is still not converted, the process can be repeated a specified number of times before a defibrillation shock is employed.

Figure 2:
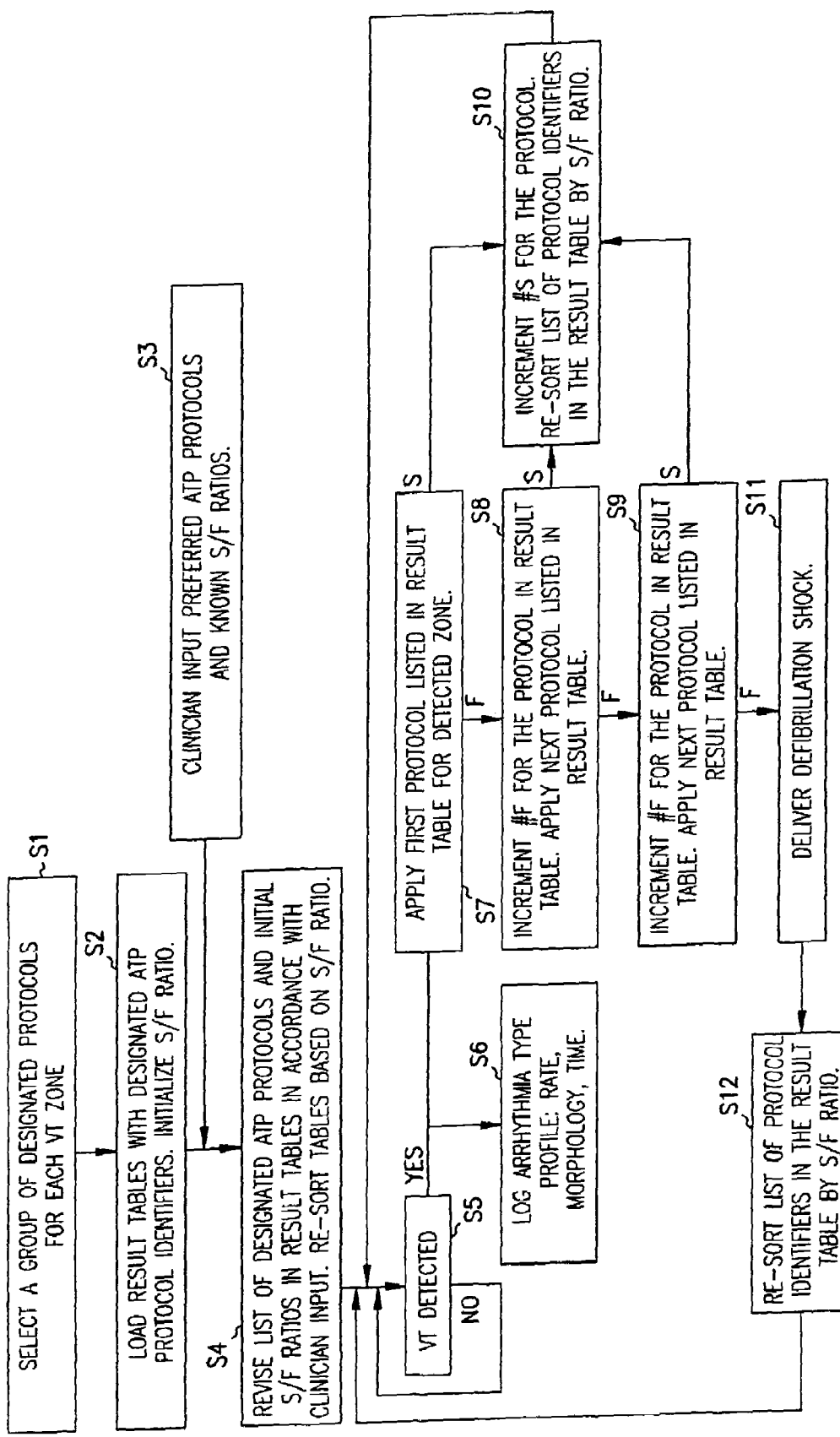
FIG. 2 is a flow diagram showing the steps performed in one implementation of the present method.

FIG. 2 shows a flow diagram of the steps performed in one particular implementation of the invention for the detection and treatment of ventricular arrhythmias. Steps S1 through S4 are configuration steps involved in setting up the device for operation, while steps S5 through S12 are performed by the microprocessor under programmed control. At step S1, a group of ATP protocols are designated for each VT subzone (i.e., arrhythmia type). The corresponding identifiers for the designated protocols are then stored in the result tables for each VT subzone at step S2, and the S/F (success/failure) ratios are initialized. A clinician may input a different choice of designated protocols for each VT subzone as well as the initial S/F ratio values at step S3. At step S4 in this embodiment, the list of protocols in the result tables and S/F ratios are revised in accordance with clinician input, and the list for each VT subzone is re-sorted based on the S/F ratio. Monitoring for terminable arrhythmias is performed at step S5. If a VT is detected, it is typed as falling within a particular VT subzone, and an arrhythmia profile is logged at step S6. The ATP protocol at the top of the list in the result table for the detected VT subzone is selected and applied at step S7. If the ATP therapy with the selected protocol fails to terminate the arrhythmia, the failure counter for that protocol is incremented at step S8, and the next protocol listed in the result table is selected and applied. If the attempt at ATP therapy with the new protocol also fails, the failure counter for that protocol is incremented, and another protocol is selected from the list and applied at step S9. If that ATP therapy attempt fails, a defibrillation shock is delivered at step S11. If the arrhythmia is successfully terminated at any of the steps S7 through S9, the success counter for the protocol employed is incremented at step S10, the protocol list in the result table is re-sorted based on S/F ratios, and the system returns to monitoring at step S5. The protocol list is also re-sorted at step S12 after termination of an arrhythmia by a defibrillation shock before returning to monitoring.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for operating a cardiac device capable of delivering a plurality of therapies for each of a plurality of ventricular tachyarrhythmia types; the method comprising:
   sensing a cardiac electrical signal of an arrhythmia episode;
   measuring a cardiac rate of the sensed cardiac electrical signal;
   determining that the measured cardiac rate exceeds a tachyarrhythmia threshold rate;
   distinguishing between a tachycardia rate zone and a fibrillation rate zone using a fibrillation rate boundary;
   if the measured cardiac rate falls within the tachycardia rate zone, then:
      analyzing a morphology of the cardiac signal;
      further classifying the arrhythmia episode as one of a plurality of types of ventricular tachyarrhythmia (VT) based on the morphology analysis;
   if the measured cardiac rate falls within the fibrillation rate zone, then:
      initially classifying the arrhythmia episode as ventricular fibrillation (VF) based on the measured cardiac rate falling within the fibrillation rate zone;
      analyzing the morphology of the cardiac signal;
      based on the morphology analysis, either (a) maintaining the classification of the arrhythmia episode as VF, or (b) reclassifying the arrhythmia episode as a ventricular tachyarrhythmia (VT) that is terminable using anti-tachyarrhythmia pacing (ATP);
   if the arrhythmia episode is classified as one of the plurality of types of VT or as the VT that is terminable using ATP, then selecting a therapy from the plurality of therapies for the type of the VT based on a history of success of the selected therapy at terminating the type of the VT, and delivering the selected therapy; and
   if the arrhythmia episode is classified as VF, then delivering a cardioversion/defibrillation shock to terminate the VF.

2. The method of claim 1, wherein analyzing the morphology of the cardiac signal is carried out using correlation.

3. The method of claim 1, wherein analyzing the morphology of the cardiac signal is carried out using frequency domain analysis.

4. The method of claim 1, further comprising determining a measure of the history of success for each of the plurality therapies for the type of the VT.

5. The method of claim 4, further comprising updating the measure of the history of success of the selected therapy based on success or failure of the selected therapy at terminating the VT.

6. The method of claim 4, wherein:
   the plurality of therapies comprises a plurality of anti-tachycardia pacing (ATP) therapies; and
   the measure of the history of success for each ATP therapy comprises a success/failure ratio.

7. The method of claim 6, wherein:
   selecting the therapy comprises selecting a first therapy having a greater success/failure relative to other therapies, and further comprising delivering a therapy having a next greatest success/failure ratio if the first selected therapy fails to terminate the VT.

8. The method of claim 6, further comprising revising the success/failure ratio of each ATP therapy based on input by a clinician.

9. The method of claim 1, further comprising revising the plurality of therapies for each type of VT based on input by a clinician.

10. A cardiac rhythm management device, comprising:
    a sensing unit configured to sense a cardiac electrical signal of an arrhythmia episode;
    a pulse generator configured to deliver a plurality of therapies for each of a plurality of ventricular tachyarrhythmia (VT) types; and
    a control processor configured to:
       measure a cardiac rate of the sensed cardiac signal;
       determine that the measured cardiac rate exceeds a tachyarrhythmia threshold rate;
       distinguish between a tachycardia rate zone and a fibrillation rate zone using a fibrillation rate boundary;
       analyze a morphology of the cardiac signal and further classify the arrhythmia episode as one of the plurality of VT types based on the morphology analysis, if the measured cardiac rate falls within the tachycardia rate zone;
       initially classify the arrhythmia episode as ventricular fibrillation (VF) based on the measured cardiac rate falling within a fibrillation rate zone; analyze the morphology of the cardiac signal; and, based on the morphology analysis, either (a) maintain the classification of the arrhythmia episode as VF, or (b) reclassify the arrhythmia episode as a VT that is terminable using anti-tachyarrhythmia pacing (ATP) if the measured cardiac rate falls within the fibrillation zone;
       select a therapy deliverable via the pulse generator to terminate the VT, the selection based on a history of success of the selected therapy at terminating the type of the VT, if the arrhythmia episode is classified as one of the plurality of types of VT or as the VT that is terminable using ATP; and
       select a cardioversion/defibrillation shock therapy to terminate the VF if the arrhythmia episode is classified as VF.

11. The device of claim 10, wherein the plurality of therapies comprises a plurality of ATP therapies for each of the plurality of VT types.

12. The device of claim 10, wherein a first selected therapy comprises ATP and the pulse generator is further configured to deliver one or both of cardioversion energy and defibrillation energy to the heart in response to failure of the selected ATP to convert the VT.

13. The device of claim 10, wherein the control processor is configured to select a plurality of ATP therapies to treat the type of VT.

14. The device of claim 10, wherein the control processor is configured to determine the type of the VT based on the morphology of the cardiac signal and the cardiac rate.

15. The device of claim 10, wherein the control processor is configured to determine the type of the VT based on morphology of the cardiac signal using correlation.

16. The device of claim 10, further comprising a memory coupled to the control processor, the memory configured to store a measure of the history of success for each of the plurality of therapies.

17. The device of claim 16, wherein the control processor is configured to revise the measure of the history of success for each of the plurality of therapies based on clinician input.

18. A cardiac device capable of delivering a plurality of tachyarrhythmia therapies for each of a plurality of ventricular tachyarrhythmia (VT) types, comprising:

a sensing system configured to sense a cardiac electrical signal of an arrhythmia episode;

means for measuring a cardiac rate of the sensed cardiac electrical signal;

means for determining that the measured cardiac rate exceeds a tachyarrhythmia threshold rate;

means for distinguishing between a tachycardia rate zone and a fibrillation rate zone using a fibrillation rate boundary;

means for (a) analyzing a morphology of the cardiac signal and (b) further classifying the arrhythmia episode as one of a plurality of types of VT based on the morphology analysis, if the measured cardiac rate falls within the tachycardia rate zone;

means for: (a) initially classifying the arrhythmia episode as ventricular fibrillation (VF) in response to the measured rate of the arrhythmia episode falling within the fibrillation rate zone; (b) analyzing the morphology of the cardiac signal; and (c) based on the morphology analysis, either (i) maintaining the classification of the arrhythmia episode as VF, or (ii) reclassifying the arrhythmia episode as a VT that is terminable using anti-tachyarrhythmia pacing (ATP), if the measured cardiac rate falls within the fibrillation rate zone;

means for selecting, if the arrhythmia episode is classified as one of the plurality of types of VT or as the VT that is terminable using ATP, a therapy from the plurality of therapies to treat the VT based on a measure of history of success of the selected therapy at terminating the type of the VT;

means for selecting, if the arrhythmia episode is classified as VF, a cardioversion/defibrillation shock to terminate the VF; and a pulse generator configured to deliver the selected therapy.

19. The device of claim 18, wherein the plurality of tachyarrhythmia therapies for each of the plurality of VT types comprises a plurality of ATP therapies for each of a plurality of VT types, wherein the VT types fall within the same cardiac rate zone and have different cardiac signal morphologies.

20. The device of claim 18, further comprising means for revising a success/failure ratio for the selected therapy based on input from a clinician.

\* \* \* \* \*

UNITED STATES PATENT AND TRADEMARK OFFICE
CERTIFICATE OF CORRECTION

PATENT NO. : 7,729,762 B2  Page 1 of 1
APPLICATION NO. : 11/267071
DATED : June 1, 2010
INVENTOR(S) : Sun et al.

It is certified that error appears in the above-identified patent and that said Letters Patent is hereby corrected as shown below:

In the Specification:

Col. 1, line 32: "dangerous tachyarrythmias," should read --dangerous tachyarrhythmias,--.

In the Claims:

Column 8, Claim 10, line 49: "pacing (ATP) if the" should be --pacing (ATP), if the--.

Signed and Sealed this

Twenty-first Day of December, 2010

David J. Kappos
*Director of the United States Patent and Trademark Office*